United States Patent [19]

Maurer et al.

[11] 4,059,696
[45] Nov. 22, 1977

[54] PYRIMIDINE (4,6)DIYL-BIS-(THIONO)(THIOL)-PHOSPHORIC(PHOSPHONIC)ACID ESTERS

[75] Inventors: Fritz Maurer; Hans-Jochem Riebel, both of Wuppertal; Ingeborg Hammann, Cologne; Wolfgang Behrenz, Overath-Steinenbrueck; Bernhard Homeyer, Leverkusen, all of Germany

[73] Assignee: Bayer Aktiengesellschaft, Leverkusen, Germany

[21] Appl. No.: 685,241

[22] Filed: May 11, 1976

[30] Foreign Application Priority Data

May 27, 1975 Germany .............................. 2523324

[51] Int. Cl.$^2$ ........................... A01N 9/36; C07F 9/65
[52] U.S. Cl. ................................ 424/200; 260/251 P; 260/251 R; 260/260
[58] Field of Search ...................... 260/251 P; 424/200

[56] References Cited

U.S. PATENT DOCUMENTS

| | | | |
|---|---|---|---|
| 3,216,894 | 11/1965 | Lorenz et al. | 260/251 P X |
| 3,309,371 | 3/1967 | Currey et al. | 260/925 |
| 3,547,920 | 12/1970 | Fest et al. | 260/250 |

FOREIGN PATENT DOCUMENTS 95,490  2/1973  Germany

OTHER PUBLICATIONS

Reznik et al., Chemical Abstracts, 7942,445K (1973).

Primary Examiner—Ronald G. Daus
Assistant Examiner—Diana G. Rivers
Attorney, Agent, or Firm—Burgess, Dinklage & Sprung

[57] ABSTRACT

Pyrimidine (4,6)diyl-bis-(thiono)(thiol)-phosphoric (phosphonic) acid esters of the formula

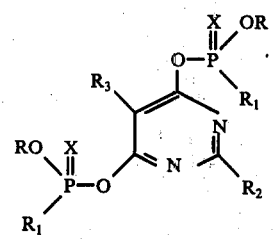

in which
R is alkyl with 1 to 6 carbon atoms,
$R_1$ is alkyl, alkoxy or alkylmercapto each with 1 to 6 carbon atoms or phenyl,
$R_2$ is alkyl, alkoxy or alkylmercapto each with 1 to 5 carbon atoms, hydrogen or phenyl,
$R_3$ is hydrogen, alkyl with 1 to 4 carbon atoms or halogen, and
X is oxygen or sulfur,
which possess insecticidal and acaricidal properties.

10 Claims, No Drawings

PYRIMIDINE (4,6)DIYL-BIS-(THIONO)(THIOL)-PHOSPHORIC(-PHOSPHONIC)ACID ESTERS

The present invention relates to and has for its objects the provision of particular new pyrimidine (4,6)diyl-bis-(thiono) (thiol)-phosphoric(phosphonic) acid esters which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that certain pyrimidinyl(thiono)-phosphoric acid esters, for example O,O-diethyl-O-[2-isopropyl-4-methylpyrimidin(6)yl]-(Compound A) and O,O-diethyl-O-[2-methyl-mercapto-4-methyl-pyrimidin(6-)yl]-thionophosphoric acid ester(Compound B) (U.S. Pat. No. 2,754,243 and German Patent Specification No. 910,652), as well as bis-(thiono)-phosphoric acid esters, for example 4,4'-dihydroxy-diphenylsulfide(-Compound C) and 4,4'-dihydroxy-diphenyldisulfide-O,O'-bis-thionophosphoric acid O,O-diethyl ester(Compound D) (German Patent Specification Nos. 1,170,401, 1,197,878), possess insecticidal and acaricidal properties.

The present invention provides pyrimidine(4,6)diyl-bis(thiono)(thiol)phosphoric(phosphonic) acid esters of the general formula

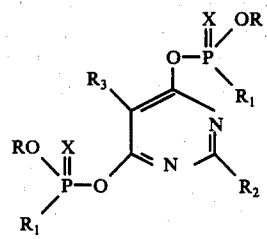

in which
R is alkyl with 1 to 6 carbon atoms,
$R_1$ is alkyl, alkoxy or alkylmercapto each with 1 to 6 carbon atoms or phenyl,
$R_2$ is alkyl, alkoxy or alkylmercapto each with 1 to 5 carbon atoms, hydrogen or phenyl,
$R_3$ is hydrogen, alkyl with 1 to 4 carbon atoms or halogen, and
X is oxygen or sulfur.

Preferably R is straight-chain or branched alkyl with 1 to 5 carbon atoms, $R_1$ is alkyl, alkoxy or alkylmercapto each with 1 to 5 carbon atoms, or phenyl, $R_2$ is straight-chain or branched alkyl, alkoxy or alkylmercapto each with 1 to 4 carbon atoms, hydrogen or phenyl, and $R_3$ is hydrogen, straight-chain or branched alkyl with 1 to 3 carbon atoms, fluorine, chlorine, bromine or iodine.

Surprisingly, the pyrimidine(4,6)diyl-bis-(thiono)(thiol)phosphoric(phosphonic) acid esters according to the invention exhibit a better leaf-insecticidal and soil-insecticidal action, and a better acaricidal action, than the corresponding compounds of analogous structure and of the same type of action previously known from the art. Accordingly, the products according to the present invention represent a genuine enrichment of the art.

The invention also provides a process for the production of a pyrimidine (4,6)diyl-bis-(thiono)(thiol)phosphoric (phosphonic) acid ester of the formula (I) in which a (thiono) (thiol)phosphoric(phosphonic)acid ester halide of the general formula

in which
R, $R_1$ and X have the abovementioned meanings and Hal denotes halogen, preferably chlorine,
is reacted with a 4,6-dihydroxypyrimidine derivative of the formula

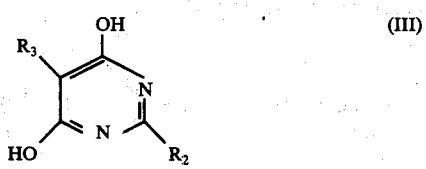

in which
$R_2$ and $R_3$ have the abovementioned meanings,
in the presence of an acid acceptor, or in the form of a dialkali metal salt, dialkaline earth metal salt or diammonium salt.

If, for example, O,O-diethyl-thionophosphoric acid diester chloride and 2-isopropyl-4,6-dihydroxy-5-chloropyrimidine are used as starting materials, the course of the reaction can be represented by the following formula scheme:

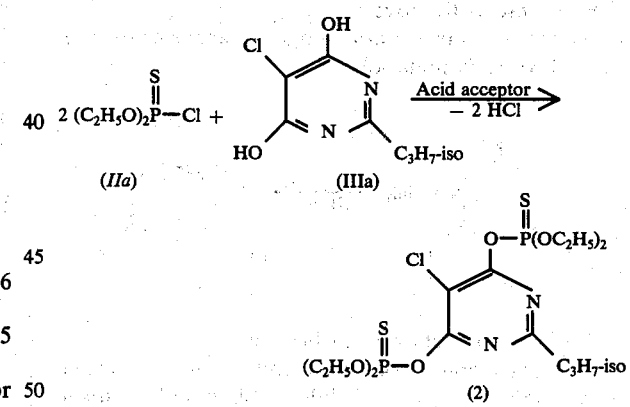

The (thiono)(thiol)phosphoric(phosphonic) acid ester halides (II) to be used as starting materials are known from the literature and can be prepared in accordance with generally customary processes.

The following may be mentioned as individual examples: O,O-dimethyl-, O,O-diethyl-, O,O-di-n-propyl-, O,O-di-iso-propyl-, O,O-di-n-butyl-, O,O-di-iso-butyl-, O,O-di-sec.- butyl and O,O-di-tert.-butyl-phosphoric acid ester chloride and the corresponding thiono analogues, as well as O-ethyl-, O-n-propyl-, O-iso-propyl-, O-n-butyl-, O-iso-butyl-, O-sec.- butyl-, O-tert.-butyl-, O-n-pentyl-, O-n-hexyl-, O-n-heptyl-, O-n-octyl- and O-n-nonyl-O-methyl- and -O-ethyl-phosphoric acid ester chloride and the corresponding thiono analogues, and also O-methyl-, -ethyl-, O-n-propyl-, O-iso-propyl-, O-n-butyl-, O-sec.-butyl-, O-iso-butyl- and O-tert.-butyl-methane-, -ethane-, -n-propane-, -iso-propane-, -butane- and -benzene-phosphonic acid ester chloride and the corresponding thiono analogues, as well as O,S-dimethyl-, O,S-diethyl-, O,S-di-n-propyl-, O,S-di-iso-propyl-, O,S-di-n-butyl-, O,S-di-iso-butyl-, O,S-di-sec.-butyl-, O,S-di-tert.-butyl-, O-methyl-S-ethyl-, O-ethyl-S-methyl-, O-ethyl-S-n-propyl- and O-ethyl-S-iso-propyl-thiolphosphoric acid ester chloride and the corresponding thiono analogues.

The 4,6-dihydroxypyrimidine derivatives (III), some of which are new, can be prepared in accordance with processes known from the literature, for example in accordance with one of the following three methods:

a. an optionally substituted malonic acid dialkyl ester is reacted with an amidine, isourea or thiourea derivative in the presence of a base, for example an alkali metal alcoholate, in accordance with the following reaction scheme:

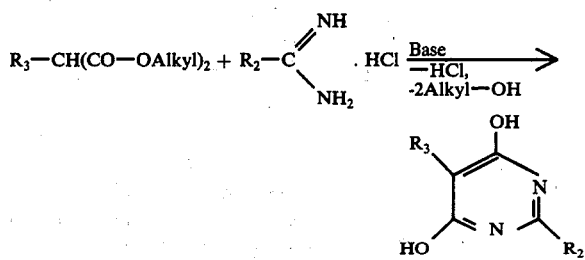

wherein
$R_2$ and $R_3$ have the abovementioned meanings, b. a 4,6-dihydroxypyrimidine derivative of the formula (III), in which
$R_2$ has the indicated meaning and
$R_3$ represents hydrogen,
is reacted with elementary halogen in accordance with the following formula scheme:

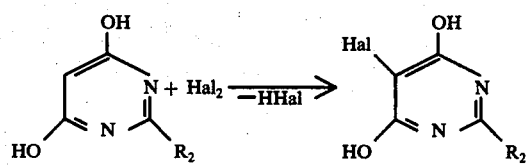

wherein
Hal represents chlorine or bromine, c. a 2-mercapto-4,6-dihydroxypyrimidine derivative is reacted with an alkyl halide or alkyl sulfate in the presence of an acid acceptor in accordance with the following formula scheme:

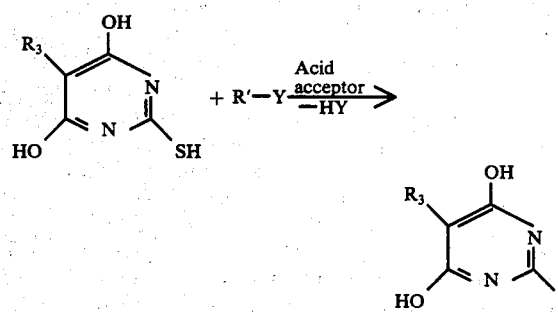

wherein
R' represents alkyl,

Y represents chlorine, bromine, iodine or alkyl-sulfate, and
$R_3$ has the abovementioned meaning.

The following may be mentioned as individual examples of the 4,6-dihydroxypyrimidine derivatives (III) to be used in accordance with the process of the invention: 4,6-dihydroxypyrimidine, 2-methyl-, 2-ethyl-, 2-n-propyl-, 2-iso-propyl-, 2-n-butyl-, 2-iso-butyl-, 2-sec.-butyl-, 2-tert.-butyl-, 2-n-pentyl-, 2-phenyl-, 2-methoxy-, 2-ethoxy-, 2-n-propoxy-, 2-iso-propoxy-, 2-n-butoxy-, 2-iso-butoxy-, 2-sec.-butoxy-, 2-tert.-butoxy-, 2-n-pentoxy-, 2-methylmercapto-, 2-ethylmercapto-, 2-n-propylmercapto-, 2-iso-propylmercapto-, 2-n-butylmercapto-, 2-iso-butylmercapto-, 2-sec.-butylmercapto-, 2-tert.-butylmercapto and 2-n-butylmercapto-4,6-dihydroxypyrimidine and also the corresponding 5-methyl, 5-ethyl, 5-n-propyl, 5-iso-propyl, 5-fluoro, 5-chloro-, 5-bromo and 5-iodo derivatives.

The reaction according to the invention is preferably carried out in the presence of a solvent, which term includes a mere diluent. Practically all inert organic solvents can be used for this purpose. These in particular include aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, and potassium tert.-butylate, have proved particularly successful, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120° C, preferably at 40° to 65° C.

In general, the reaction is allowed to take place under normal pressure.

In general, 2 moles of (thiono)(thiol)phosphoric(-phosphonic) acid ester chloride (II) are employed per mole of 4,6-dihydroxypyrimidine derivative (III) when carrying out the process. In most cases, the 4,6-dihydroxypyrimidine derivative (III) in one of the stated solvents or diluents, if appropriate together with the acid acceptor, is taken and the phosphorus component is added dropwise. After heating for from one to several hours at the stated temperatures, the reaction mixture is poured into an organic solvent, for example toluene, and worked up in the usual manner, for example by separating off the organic phase, washing and drying it and distilling off the solvent.

The new compounds are frequently obtained in the form of oils, which in most cases cannot be distilled without decomposition, but can be freed from the last volatile constituents by so-called "slight distillation", that is to say by prolonged heating under reduced pressure to moderately elevated temperatures, and they can be purified in this way. They are characterized by their refractive index. Some of the compounds are obtained in a crystalline form and have a sharp melting point.

As has already been mentioned, the pyrimidine(4,6)diylbis-(thiono)(thiol)phosphoric(phosphonic) acid esters according to the invention are distinguished by an excellent leaf-insecticidal and soil-insecticidal activity and acaricidal activity. They are active against plant pests, hygiene pests and pests of stored products. They have a good action against both sucking and biting insects and mites.

For this reason, the compounds according to the invention can be employed successfully as pesticides in plant protection and in the hygiene field and the field of protection of stored products.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry blackfly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*) the blossom beetle (*Meligethes aeneus*), the raspberry bettle (*Byturus tomentosus*), the bean weevil (*Bruchidius = Acanthoscelides obtectus*), the leather bettle (*Dermestes frischi*), the khapra bettle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*). With the mites (*Acari*) there are classed, in particular, the spider mites (*Tetranychidae*) such as the two-spotted spider mite (*Tetranychus urticae*) and the European rod mite (*Paratetranychus pilosus = Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to a area where a crop is to be grown or to a domestic animal, a correspondingly combative or toxic amount, i.e. insecticidally or acaricidally effective amount, of the particular active compound of the invention along or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Plutella* test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified period of time, the degree of destruction was determined as a percentage: 100% means that all the caterpillars were killed whereas 0% means that none of the caterpillers were killed.

The active compounds, the concentrations of the active compounds, the evaluation times and the results can be seen from the following Table 1:

Table 1
(Plutella test)

| Active compound | Active compound concentration in % by wt. | Degree of destruction in % after 3 days |
|---|---|---|
| $\left( (C_2H_5O)_2\overset{S}{\underset{\parallel}{P}}-O-\!\!\!\left\langle\!\!\!\begin{array}{c}\phantom{x}\\\phantom{x}\end{array}\!\!\!\right\rangle\!\!\!-S \right)_2$ (known) (D) | 0.1<br>0.01 | 100<br>0 |
| structure with $S, OC_2H_5, O-P, OC_2H_5, N, CH_3S, N, CH_3$ (known) (B) | 0.1<br>0.01 | 100<br>0 |

Table 1-continued (Plutella test)

| Active compound | Active compound concentration in % by wt. | Degree of destruction in % after 3 days |
|---|---|---|
| Structure with pyrimidine, two O-P(=S)(OCH$_3$)$_2$ groups (45) | 0.1 / 0.01 | 100 / 100 |
| CH$_3$S-substituted pyrimidine with two O-P(=S)(OCH$_3$)$_2$ groups (43) | 0.1 / 0.01 | 100 / 100 |
| C$_2$H$_5$-substituted pyrimidine with two O-P(=S)(OCH$_3$)$_2$ groups (41) | 0.1 / 0.01 | 100 / 100 |
| C$_2$H$_5$O-substituted pyrimidine with two O-P(=S)(OCH$_3$)$_2$ groups (19) | 0.1 / 0.01 | 100 / 100 |
| iC$_3$H$_7$-substituted pyrimidine with two O-P(=S)(OCH$_3$)$_2$ groups (33) | 0.1 / 0.01 | 100 / 100 |

Table 1-continued (Plutella test)

| Active compound | Active compound concentration in % by wt. | Degree of destruction in % after 3 days |
|---|---|---|
| CH$_3$-substituted pyrimidine with two O-P(=S)(OCH$_3$)(C$_2$H$_5$) groups (29) | 0.1 / 0.01 | 100 / 100 |
| CH$_3$O-substituted pyrimidine with two O-P(=S)(OCH$_3$)(C$_2$H$_5$) groups (26) | 0.1 / 0.01 | 100 / 100 |
| C$_2$H$_5$-substituted pyrimidine with two O-P(=S)(OCH$_3$)(OC$_3$H$_7$) groups (40) | 0.1 / 0.01 | 100 / 100 |
| iC$_3$H$_7$O-substituted, CH$_3$-substituted pyrimidine with two O-P(=S)(OCH$_3$)(OC$_3$H$_7$) groups (56) | 0.1 / 0.01 | 100 / 100 |
| Pyrimidine with two O-P(=S)(OC$_2$H$_5$)$_2$ groups (25) | 0.1 / 0.01 | 100 / 100 |

Table 1-continued
(Plutella test)

| Active compound | Active compound concentration in % by wt. | Degree of destruction in % after 3 days |
|---|---|---|
| (28) CH₃-pyrimidine with O-P(S)(OC₂H₅)₂ groups | 0.1<br>0.01 | 100<br>100 |
| (53) CH₃-pyrimidine with CH₃ and O-P(S)(OC₂H₅)₂ groups | 0.1<br>0.01 | 100<br>100 |
| (61) CH₃-pyrimidine with CH₃ and O-P(O)(OC₂H₅)₂ groups | 0.1<br>0.01 | 100<br>100 |
| (52) CH₃-pyrimidine with Cl and O-P(S)(OC₂H₅)₂ groups | 0.1<br>0.01 | 100<br>100 |
| (65) CH₃-pyrimidine with Cl and O-P(O)(OC₂H₅)₂ groups | 0.1<br>0.01 | 100<br>100 |

Table 1-continued
(Plutella test)

| Active compound | Active compound concentration in % by wt. | Degree of destruction in % after 3 days |
|---|---|---|
| (5) CH₃S-pyrimidine with O-P(S)(OC₂H₅)₂ groups | 0.1<br>0.01 | 100<br>100 |
| (16) CH₃S-pyrimidine with O-P(O)(OC₂H₅)₂ groups | 0.1<br>0.01 | 100<br>100 |
| (21) CH₃O-pyrimidine with O-P(S)(OC₂H₅)₂ groups | 0.1<br>0.01 | 100<br>100 |
| (42) C₂H₅-pyrimidine with O-P(S)(OC₂H₅)₂ groups | 0.1<br>0.01 | 100<br>100 |
| (1) C₂H₅O-pyrimidine with O-P(S)(OC₂H₅)₂ groups | 0.1<br>0.01 | 100<br>100 |

Table 1-continued
(Plutella test)
| Active compound | Active compound concentration in % by wt. | Degree of destruction in % after 3 days |
|---|---|---|
| 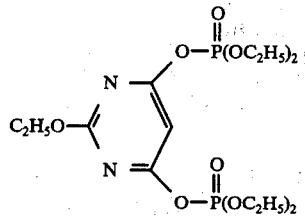 (10) | 0.1<br>0.01 | 100<br>100 |
| 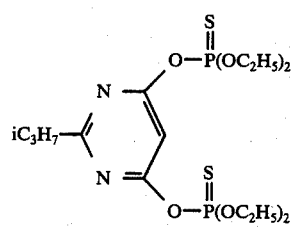 (3) | 0.1<br>0.01 | 100<br>100 |
| 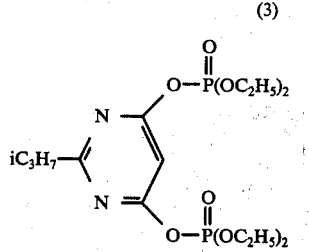 (7) | 0.1<br>0.01 | 100<br>100 |
| 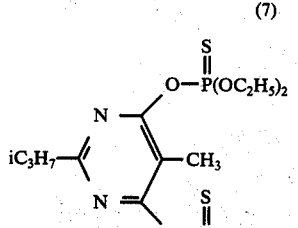 (54) | 0.1<br>0.01 | 100<br>100 |
| 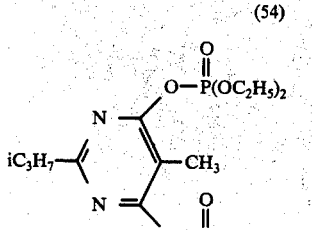 (58) | 0.1<br>0.01 | 100<br>100 |
Table 1-continued
(Plutella test)
| Active compound | Active compound concentration in % by wt. | Degree of destruction in % after 3 days |
|---|---|---|
| 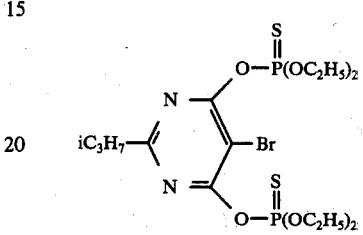 (17) | 0.1<br>0.01 | 100<br>100 |
| 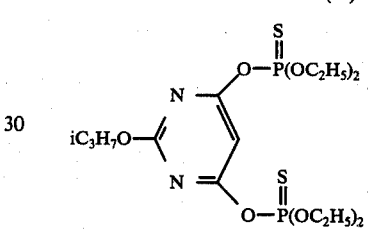 (35) | 0.1<br>0.01 | 100<br>100 |
| 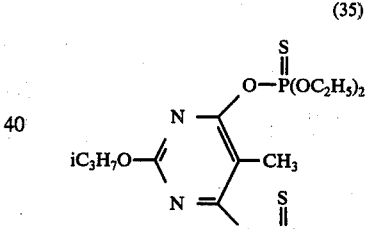 (48) | 0.1<br>0.01 | 100<br>100 |
| 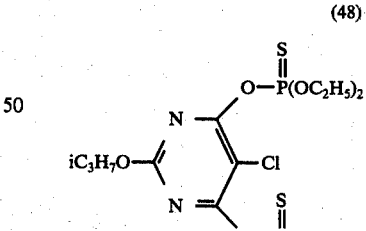 (2) | 0.1<br>0.01 | 100<br>100 |
| 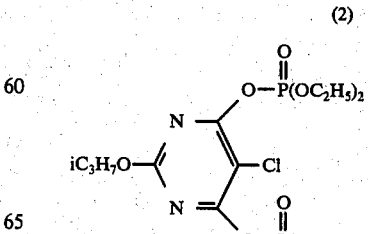 (63) | 0.1<br>0.01 | 100<br>100 |

Table 1-continued (Plutella test)

| Active compound | Active compound concentration in % by wt. | Degree of destruction in % after 3 days |
|---|---|---|
| (14) structure with CH substituent, pyrimidine bearing two O-P(=S)(OC$_2$H$_5$)(C$_2$H$_5$) groups | 0.1<br>0.01 | 100<br>100 |
| (24) pyrimidine with CH$_3$, two O-P(=S)(OC$_2$H$_5$)(C$_2$H$_5$) groups | 0.1<br>0.01 | 100<br>100 |
| (23) pyrimidine with CH$_3$ and CH$_3$, two O-P(=S)(OC$_2$H$_5$)(C$_2$H$_5$) groups | 0.1<br>0.01 | 100<br>100 |
| (60) pyrimidine with CH$_3$ and Cl, two O-P(=S)(OC$_2$H$_5$)(C$_2$H$_5$) groups | 0.1<br>0.01 | 100<br>100 |
| (64) pyrimidine with CH$_3$S and Cl, two O-P(=S)(OC$_2$H$_5$)(C$_2$H$_5$) groups | 0.1<br>0.01 | 100<br>100 |

Table 1-continued (Plutella test)

| Active compound | Active compound concentration in % by wt. | Degree of destruction in % after 3 days |
|---|---|---|
| (18) pyrimidine with CH$_2$O, two O-P(=S)(OC$_2$H$_5$)(C$_2$H$_5$) groups | 0.1<br>0.01 | 100<br>100 |
| (22) pyrimidine with C$_2$H$_5$, two O-P(=S)(OC$_2$H$_5$)(C$_2$H$_5$) groups | 0.1<br>0.01 | 100<br>100 |
| (38) pyrimidine with C$_2$H$_5$O, two O-P(=S)(OC$_2$H$_5$)(C$_2$H$_5$) groups | 0.1<br>0.01 | 100<br>100 |
| (11) pyrimidine with iC$_3$H$_7$, two O-P(=S)(OC$_2$H$_5$)(C$_2$H$_5$) groups | 0.1<br>0.01 | 100<br>100 |
| (4) pyrimidine with iC$_3$H$_7$ and Br, two O-P(=S)(OC$_2$H$_5$)(C$_2$H$_5$) groups | 0.1<br>0.01 | 100<br>100 |

Table 1-continued
(Plutella test)

| Active compound | Active compound concentration in % by wt. | Degree of destruction in % after 3 days |
|---|---|---|
| (36) | 0.1 | 100 |
|  | 0.01 | 100 |
| (50) | 0.1 | 100 |
|  | 0.01 | 100 |
| (15) | 0.1 | 100 |
|  | 0.01 | 100 |
| (27) | 0.1 | 100 |
|  | 0.01 | 100 |
| (39) | | |
| (12) | 0.1 | 100 |
|  | 0.01 | 100 |
| (9) | 0.1 | 100 |
|  | 0.01 | 100 |
| (59) | 0.1 | 100 |
|  | 0.01 | 100 |
| (37) | 0.1 | 100 |
|  | 0.01 | 100 |
| (8) | | |

Table 1-continued
(Plutella test)

| Active compound | Active compound concentration in % by wt. | Degree of destruction in % after 3 days |
|---|---|---|
| (51) | 0.1 / 0.01 | 100 / 100 |
| (34) | 0.1 / 0.01 | 100 / 100 |
| (20) | 0.1 / 0.01 | 100 / 100 |
| (70) | 0.1 / 0.01 | 100 / 100 |
| (79) | 0.1 / 0.01 | 100 / 100 |
| (75) | 0.1 / 0.01 | 100 / 100 |
| (72) | 0.1 / 0.01 | 100 / 100 |
| (64) | 0.1 / 0.01 | 100 / 100 |
| (71) | 0.1 / 0.01 | 100 / 100 |
| (82) | 0.1 / 0.01 | 100 / 100 |

Table 1-continued
(Plutella test)

| Active compound | Active compound concentration in % by wt. | Degree of destruction in % after 3 days |
|---|---|---|
| (85) | 0.1<br>0.01 | 100<br>100 |
| (67) | 0.1<br>0.01 | 100<br>100 |
| (66) | 0.1<br>0.01 | 100<br>100 |
| (76) | 0.1<br>0.01 | 100<br>100 |
| (83) | 0.1<br>0.01 | 100<br>100 |
| (80) | 0.1<br>0.01 | 100<br>100 |
| (77) | 0.1<br>0.01 | 100<br>100 |
| (73) | 0.1<br>0.01 | 100<br>100 |
| (81) | 0.1<br>0.01 | 100<br>100 |

Table 1-continued (Plutella test)

| Active compound | Active compound concentration in % by wt. | Degree of destruction in % after 3 days |
|---|---|---|
| [structure: pyrimidine with two O-P(=S)(OCH₃)(C₂H₅) groups] | 0.1<br>0.01 | 100<br>100 |
| [structure: CH₃S-pyrimidine with two O-P(=S)(OCH₃)(C₂H₅) groups] | 0.1<br>0.01 | 100<br>100 |

(19)

EXAMPLE 2

*Myzus* test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds in % by weight, the evaluation times and the results can be seen from the following Table 2:

Table 2

(Myzus test)

| Active compound | Active compound concentration in % | Degree of destruction in % after 1 day |
|---|---|---|
| $((C_2H_5O)_2P(=S)-O-C_6H_4-S-)_2$ (known) (D) | 0.1 | 0 |
| $(C_2H_5O)_2P(=S)-O-C_6H_4-S-C_6H_4-O-P(=S)(OC_2H_5)_2$ (known) (C) | 0.1<br>0.01 | 100<br>0 |
| [pyrimidine with (CH₃)₂CH–, CH₃, and O-P(=S)(OC₂H₅)₂ substituents] (known) (A) | 0.01<br>0.001<br>0.0001 | 100<br>40<br>0 |
| [pyrimidine with C₂H₅O–, O-P(=S)(OCH₃)₂, and O-P(=S)(OCH₃)₂ substituents] | 0.01<br>0.001<br>0.0001 | 100<br>100<br>80 |

Table 2-continued
(Myzus test)

| Active compound | Active compound concentration in % | Degree of destruction in % after 1 day |
|---|---|---|
| (structure with S/OCH₃, C₂H₅ groups on pyrimidine with CH₃) | 0.01<br>0.001<br>0.0001 | 100<br>100<br>50 |
| (29) (structure with OCH₃, OC₃H₇ groups on pyrimidine with C₂H₅) | 0.01<br>0.001<br>0.0001 | 100<br>80<br>30 |
| (40) (structure with O-P(OC₂H₅)₂ groups on pyrimidine with CH₃) | 0.01<br>0.001<br>0.0001 | 100<br>99<br>95 |
| (28) (structure with O-P(OC₂H₅)₂ groups on pyrimidine with CH₃O) | 0.01<br>0.001<br>0.0001 | 100<br>100<br>99 |
| (21) (structure with O-P(OC₂H₅)₂ groups on pyrimidine with C₂H₅) | 0.01<br>0.001<br>0.0001 | 100<br>99<br>70 |
| (42) (structure with O-P(OC₂H₅)₂ groups on pyrimidine with C₂H₅O) | 0.01<br>0.001<br>0.0001 | 100<br>95<br>90 |
| (1) | | |

Table 2-continued
(Myzus test)

| Active compound | Active compound concentration in % | Degree of destruction in % after 1 day |
|---|---|---|
| (23) [2-methyl-pyrimidine-4,6-diyl bis(O-ethyl ethylphosphonothioate)] | 0.01<br>0.001<br>0.0001 | 100<br>100<br>80 |
| (14) [2-methylthio-pyrimidine-4,6-diyl bis(O-ethyl ethylphosphonothioate)] | 0.01<br>0.001<br>0.0001 | 100<br>97<br>30 |
| (22) [2-methoxy-pyrimidine-4,6-diyl bis(O-ethyl ethylphosphonothioate)] | 0.01<br>0.001<br>0.0001 | 100<br>99<br>55 |
| (38) [2-ethyl-pyrimidine-4,6-diyl bis(O-ethyl ethylphosphonothioate)] | 0.01<br>0.001<br>0.0001 | 100<br>99<br>90 |
| (36) [2-isopropyl-pyrimidine-4,6-diyl bis(O-ethyl ethylphosphonothioate)] | 0.01<br>0.001<br>0.0001 | 100<br>100<br>50 |

Table 2-continued (Myzus test)

| Active compound | Active compound concentration in % | Degree of destruction in % after 1 day |
|---|---|---|
| (39) | 0.01<br>0.001<br>0.0001 | 100<br>99<br>50 |
| (12) | 0.01<br>0.001<br>0.0001 | 100<br>85<br>50 |
| (9) | 0.01<br>0.001<br>0.0001 | 100<br>99<br>40 |
| (27) | 0.01<br>0.001<br>0.0001 | 100<br>99<br>50 |
| (69) | 0.01<br>0.001<br>0.0001 | 100<br>95<br>55 |

Table 2-continued

| Active compound | (Myzus test) Active compound concentration in % | Degree of destruction in % after 1 day |
| --- | --- | --- |
| [Structure with C₂H₅ group, N=, O-P(=S)(CH₃)(OC₂H₅) groups] | 0.01<br>0.001<br>0.0001 | 100<br>100<br>55 |
| (71) [Structure with CH₃S group, N=, O-P(=S)(OCH₃)(C₂H₅) groups] | 0.01<br>0.001<br>0.0001 | 100<br>100<br>85 |
| (68) [Structure with C₂H₅ group, N=, O-P(=S)(OCH₃)(C₂H₅) groups] | 0.01<br>0.001<br>0.0001 | 100<br>100<br>85 |
| (70) [Structure with iC₃H₇ group, N=, O-P(=S)(OCH₃)(C₂H₅) groups] | 0.01<br>0.001<br>0.0001 | 100<br>100<br>99 |
| (79) | | |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10-30 cm, were sprayed with the preparation of the active compound until dripping wet. These bean plants were heavily infested with the common or two-spotted spider mite (*Tetranychus urticae*) in all stages of development.

After the specified periods of time, the degree of desctruction was determined as a percentage: 100% means that all the spider mites were killed whereas 0% means that none of the spider mites were killed.

The active compounds, the concentrations of the active compounds in % by weight, the evaluation times and the results can be seen from the following table 3:

Table 3
(Tetranychus test)

| Active compound | Active compound concentration in % | Degree of destruction in % after 2 days |
|---|---|---|
| [(C₂H₅O)₂P(S)-O-C₆H₄-S]₂ (known) (D) | 0.1 | 0 |
| 4-(diethoxyphosphinothioyloxy)-2-methylthio-6-methylpyrimidine (known) (B) | 0.1 | 0 |
| 4-(diethoxyphosphinothioyloxy)-2-isopropyl-6-methylpyrimidine (known) (A) | 0.1 0.01 | 95 0 |
| 4-(diethoxyphosphinothioyloxy)-2-isopropylthio-6-methylpyrimidine (known) (E) | 0.1 | 0 |
| Compound (19) — 2-ethoxy-4,6-bis(dimethoxyphosphinothioyloxy)pyrimidine | 0.1 0.01 | 100 98 |
| Compound (23) — 2-methyl-4,6-bis(ethoxy(ethyl)phosphinothioyloxy)pyrimidine | 0.1 0.01 | 99 99 |
| Compound (38) — 2-ethyl-4,6-bis(ethoxy(ethyl)phosphinothioyloxy)pyrimidine | 0.1 0.01 | 100 98 |
| Compound (39) — 2-ethyl-4,6-bis(isopropoxy(methyl)phosphinothioyloxy)pyrimidine | 0.1 0.01 | 100 100 |
| Compound (9) — 2-isopropyl-4,6-bis(isopropoxy(methyl)phosphinothioyloxy)pyrimidine | 0.1 0.01 | 100 100 |
| Compound (27) — 2-methoxy-4,6-bis(isopropoxy(methyl)phosphinothioyloxy)pyrimidine | 0.1 0.01 | 100 98 |
| Compound (82) — 2-ethoxy-4,6-bis(ethoxy(methyl)phosphinothioyloxy)pyrimidine | 0.1 0.01 | 100 98 |

Table 3-continued
(Tetranychus test)

| Active compound | Active compound concentration in % | Degree of destruction in % after 2 days |
|---|---|---|
| [structure (67)] | 0.1<br>0.01 | 99<br>99 |
| [structure (66)] | 0.1<br>0.01 | 100<br>100 |
| [structure (75)] | 0.1<br>0.01 | 100<br>100 |
| [structure (72)] | 0.1<br>0.01 | 100<br>100 |
| [structure (71)] | 0.1<br>0.01 | 100<br>100 |

EXAMPLE 4

Critical concentration test/soil insects
Test insect: *Tenebrio molitor* larvae in the soil Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% is exactly as many test insects were still alive as in the case of the untreated control.

The active compounds, amounts used and results can be seen from the Table 4 which follows:

Table 4
(Soil insecticide test/*Tenebrio molitor* larvae in the soil)

| Active compound | Degree of destruction in % at an active compound concentration of 20 ppm |
|---|---|
| [structure (B) (known)] | 0 |
| [structure (10)] | 100 |
| [structure (3)] | 100 |
| [structure (4)] | 100 |

Table 4-continued
(Soil insecticide test/*Tenebrio molitor* larvae in the soil)
| Active compound | Degree of destruction in % at an active compound concentration of 20 ppm |
|---|---|
| 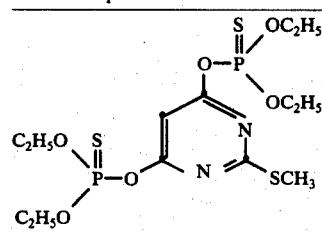 (5) | 100 |
| 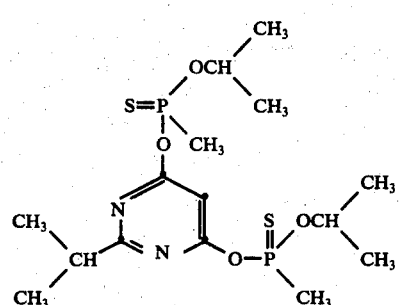 (9) | 100 |
| 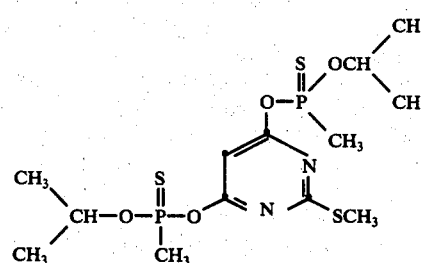 (15) | 100 |
| 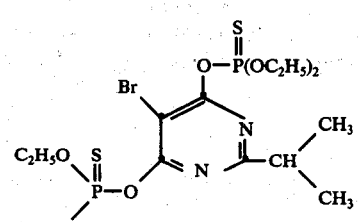 (17) | 100 |
| 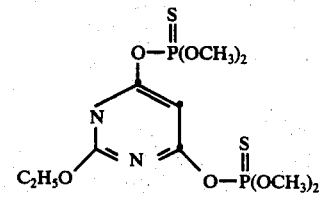 (19) | 100 |
| 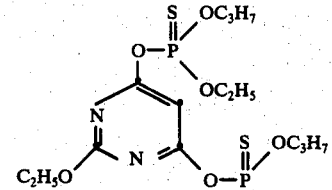 (20) | 100 |
| 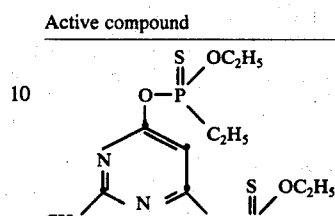 (23) | 100 |
| 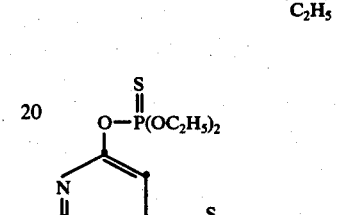 (25) | 100 |
| 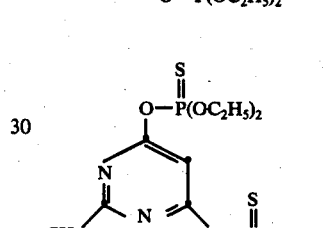 (28) | 100 |
| 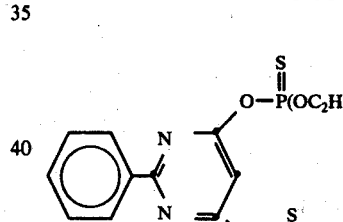 (30) | 100 |
| 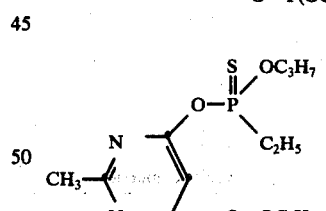 (34) | 100 |
| 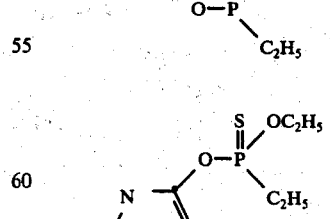 (38) | 100 |

Table 4-continued
(Soil insecticide test/*Tenebrio molitor* larvae in the soil)

| Active compound | Degree of destruction in % at an active compound concentration of 20 ppm |
|---|---|
| (39) [structure: pyrimidine with C₂H₅, two O–P(S)(OCH(CH₃)₂)(CH₃) groups] | 100 |
| (42) [structure: pyrimidine with C₂H₅, two O–P(S)(OC₂H₅)₂ groups] | 100 |
| (53) [structure: pyrimidine with CH₃, CH₃, two O–P(S)(OC₂H₅)₂ groups] | 100 |
| (2) [structure: pyrimidine with i-C₃H₇O, Cl, two O–P(S)(OC₂H₅)₂ groups] | 100 |
| (54) [structure: pyrimidine with i-C₃H₇, CH₃, two O–P(S)(OC₂H₅)₂ groups] | 100 |

EXAMPLE 5

LT$_{100}$ test for Diptera

Test insects: *Aedes aegypti*

Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there is 100% destruction can be seen from the following Table 5:

Table 5
(LT$_{100}$ test for *Diptera/Aedes aegypti*)

| Active compound | Active compound concentration of the solution in % | LT$_{100}$ in minutes (') |
|---|---|---|
| (C) (known) [bis(phenyl-O–P(S)(OC₂H₅)₂) sulfide structure] | 0.2 | 180' = 0% |
| (D) (known) [–S–C₆H₄–O–P(S)(OC₂H₅)₂]₂ | 0.2 | 180' = 0% |

Table 5-continued (LT$_{100}$ test for *Diptera/Aedes aegypti*)

| Active compound | Active compound concentration of the solution in % | LT$_{100}$ in minutes (') |
|---|---|---|
| (45) | 0.02<br>0.002 | 120'<br>180' |
| (25) | 0.2 | 120' |
| (24) | 0.2 | 120' |
| (28) | 0.02 | 120' |
| (23) | 0.02 | 180' |
| (29) | 0.02 | 120' |

Table 5-continued (LT$_{100}$ test for *Diptera/Aedes aegypti*)

| Active compound | Active compound concentration of the solution in % | LT$_{100}$ in minutes (') |
| --- | --- | --- |
| (34) | 0.2 | 120' |
| (41) | 0.2<br>0.02 | 60'<br>180' |
| (42) | 0.2<br>0.02 | 120'<br>180' |
| (40) | 0.2<br>0.02 | 120'<br>180' |
| (39) | 0.2<br>0.02 | 120'<br>180' |

Table 5-continued (LT$_{100}$ test for *Diptera/Aedes aegypti*)

| Active compound | Active compound concentration of the solution in % | LT$_{100}$ in minutes (') |
|---|---|---|
| (38) | 0.2<br>0.02 | 60'<br>180' |
| (33) | 0.2<br>0.02 | 120'<br>180' = 90% |
| (3) | 0.2<br>0.02 | 120'<br>180' = 90% |
| (4) | 0.2 | 120' |
| (7) | 0.2 | 60' |
| (21) | 0.2<br>0.02 | 120'<br>180' |

Table 5-continued
(LT$_{100}$ test for Diptera/Aedes aegypti)
| Active compound | Active compound concentration of the solution in % | LT$_{100}$ in minutes (') |
|---|---|---|
| 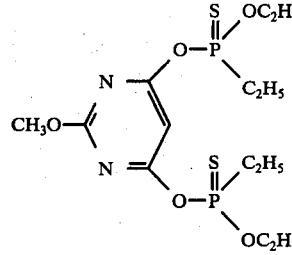 (22) | 0.2<br>0.02 | 120'<br>180' |
| 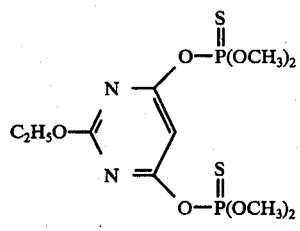 (19) | 0.2<br>0.02 | 60'<br>180' |
| 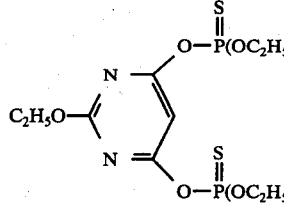 (1) | 0.<br>0.02 | 60'<br>180' |
| 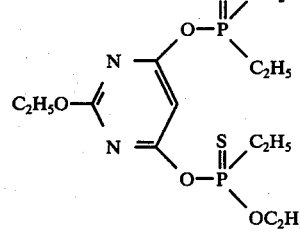 (11) | 0.2 | 120' |
| 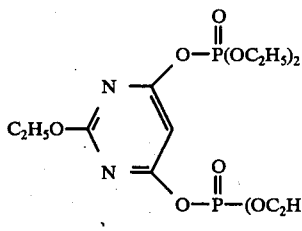 (10) | 0.2<br>0.02 | 60'<br>180' |
| 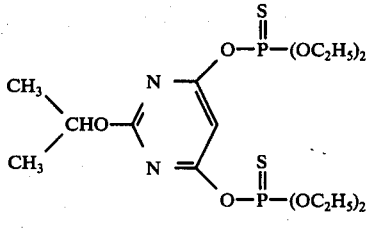 (35) | 0.2<br>0.02 | 120'<br>180' = 80% |

Table 5-continued (LT$_{100}$ test for *Diptera/Aedes aegypti*)

| Active compound | Active compound concentration of the solution in % | LT$_{100}$ in minutes (') |
|---|---|---|
| (36) | 0.2<br>0.02 | 120'<br>180' |
| (37) | 0.2<br>0.02 | 120'<br>180' = 80% |
| (43) | 0.2<br>0.02 | 120'<br>180' = 50% |
| (5) | 0.2<br>0.02 | 60'<br>120' |
| (15) | 0.2<br>0.02 | 60'<br>180' |

Table 5-continued (LT$_{100}$ test for Diptera/Aedes aegypti)

| Active compound | Active compound concentration of the solution in % | LT$_{100}$ in minutes (') |
|---|---|---|
| (14) | 0.2<br>0.02 | 60'<br>120' |
| (16) | 0.2<br>0.02 | 60'<br>180' = 80% |
| (30) | 0.2 | 120' |
| (31) | 0.2<br>0.02 | 120'<br>180' |
| (53) | 0.2<br>0.02 | 60'<br>120' |
| (60) | 0.2<br>0.02 | 60'<br>120' |

Table 5-continued
(LT$_{100}$ test for *Diptera/Aedes aegypti*)
| Active compound | Active compound concentration of the solution in % | LT$_{100}$ in minutes (') |
|---|---|---|
| 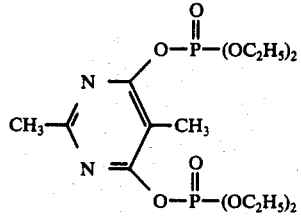 (61) | 0.2<br>0.02 | 60'<br>120' |
| 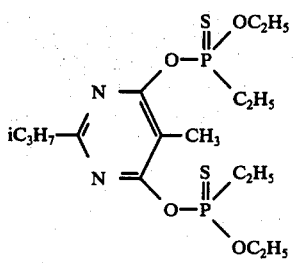 (57) | 0.2<br>0.02 | 120'<br>180' = 50% |
| 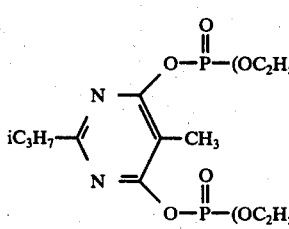 (58) | 0.2<br>0.02 | 60'<br>180' |
| 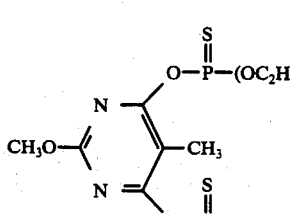 (47) | 0.2<br>0.02 | 120'<br>180' |
| 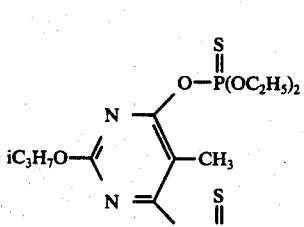 (48) | 0.2<br>0.02 | 120'<br>180' = 80% |
| 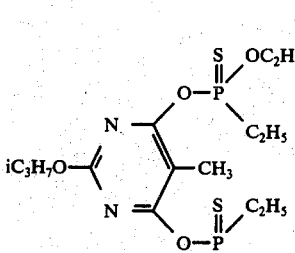 (50) | 0.2<br>0.02 | 120'<br>180' = 80% |

Table 5-continued (LT$_{100}$ test for *Diptera/Aedes aegypti*)

| Active compound | Active compound concentration of the solution in % | LT$_{100}$ in minutes (') |
|---|---|---|
| (56) | 0.2<br>0.02 | 120'<br>180' = 80% |
| (49) | 0.2<br>0.02 | 60'<br>180' = 90% |
| (52) | 0.2<br>0.02 | 60'<br>180' |
| (64) | 0.2<br>0.02 | 60'<br>120' |
| (65) | 0.2<br>0.02 | 60'<br>180' |
| (17) | 0.2<br>0.02 | 120'<br>180' = 50% |

Table 5-continued (LT$_{100}$ test for *Diptera/Aedes aegypti*)

| Active compound | Active compound concentration of the solution in % | LT$_{100}$ in minutes (') |
|---|---|---|
| (18) structure with iC$_3$H$_7$ replaced by (CH$_3$)$_2$CH–, Br substituent, and two –O–P(S)(OC$_2$H$_5$)(C$_2$H$_5$) groups | 0.2 | 120' |
| (2) structure with iC$_3$H$_7$O–, Cl substituent, two –O–P(S)(OC$_2$H$_5$)$_2$ groups | 0.2<br>0.02 | 60'<br>180' |
| (62) structure with iC$_3$H$_7$O–, Cl substituent, two –O–P(S)(OC$_2$H$_5$)(C$_2$H$_5$) groups | 0.2<br>0.02 | 120'<br>180' |
| structure with iC$_3$H$_7$O–, Cl substituent, two –O–P(O)–(OC$_2$H$_5$)$_2$ groups | 0.2<br>0.02 | 60'<br>120' |

EXAMPLE 6

LD$_{100}$ test
Test insects: *Sitophilus granarius*

Solvent: Acetone 2 parts by weight of the active compound were taken up in 1,000 parts by volume of the solvent. The solution so obtained was diluted with further solvent to the desired concentrations.

2.5 ml of the solution of the active compound was pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test animals were then placed in the Petri dish and it was covered with a glass lid.

The condition of the test animals was observed 3 days after the commencement of the experiments. The destruction, in %, was determined. 100% denotes that all test animals had been killed; 0% denotes that no test animals had been killed.

The active compounds, the concentrations of the active compounds in % by weight, the test animals and the results can be seen from the following Table 6:

Table 6

(LD$_{100}$ test/*Sitophilus granarius*)

| Active compound | Active compound concentration of the solution in % | Degree of destruction in % |
|---|---|---|
| [(C$_2$H$_5$O)$_2$–P(S)–O–C$_6$H$_4$–S]$_2$ (known) (D) | 0.2 | 0 |

Table 6-continued (LD$_{100}$ test/*Sitophilus granarius*)

| Active compound | Active compound concentration of the solution in % | Degree of destruction in % |
|---|---|---|
| (49) pyrimidine-4,6-diyl bis(O,O-dimethyl phosphorothioate) | 0.2<br>0.02 | 100<br>100 |
| (25) pyrimidine-4,6-diyl bis(O,O-diethyl phosphorothioate) | 0.2<br>0.02 | 100<br>100 |
| (24) pyrimidine-4,6-diyl bis(O-ethyl ethylphosphonothioate) | 0.2<br>0.02 | 100<br>100 |
| (28) 2-methylpyrimidine-4,6-diyl bis(O,O-diethyl phosphorothioate) | 0.2<br>0.02 | 100<br>100 |
| (23) 2-methylpyrimidine-4,6-diyl bis(O-ethyl ethylphosphonothioate) | 0.2<br>0.02 | 100<br>100 |
| (29) 2-methylpyrimidine-4,6-diyl O-methyl ethylphosphonothioate / O-methyl ethylphosphonothioate | 0.2 | 100 |
| (34) 2-methylpyrimidine-4,6-diyl bis(O-propyl ethylphosphonothioate) | 0.2<br>0.02 | 100<br>90 |
| (41) 2-ethylpyrimidine-4,6-diyl bis(O,O-dimethyl phosphorothioate) | 0.2<br>0.02 | 100<br>90 |
| (42) 2-ethylpyrimidine-4,6-diyl bis(O,O-diethyl phosphorothioate) | 0.2<br>0.02 | 100<br>100 |
| (40) 2-ethylpyrimidine-4,6-diyl bis(O-methyl O-propyl phosphorothioate) | 0.2<br>0.02 | 100<br>100 |

Table 6-continued (LD$_{100}$ test/*Sitophilus granarius*)

| Active compound | Active compound concentration of the solution in % | Degree of destruction in % |
|---|---|---|
| (39) | 0.2 / 0.02 | 100 / 100 |
| (38) | 0.2 / 0.02 | 100 / 100 |
| (33) | 0.2 / 0.02 | 100 / 100 |
| (3) | 0.2 / 0.02 | 100 / 100 |
| (9) | 0.2 / 0.02 | 100 / 90 |
| (4) | 0.2 / 0.02 | 100 / 100 |
| (8) | 0.2 | 100 |
| (7) | 0.2 | 100 |
| (21) | 0.2 / 0.02 | 100 / 100 |
| (22) | 0.2 / 0.02 | 100 / 100 |

Table 6-continued
(LD$_{100}$ test/*Sitophilus granarius*)

| Active compound | Active compound concentration of the solution in % | Degree of destruction in % |
|---|---|---|
| (26) | 0.2 / 0.02 | 100 / 70 |
| (19) | 0.2 / 0.02 | 100 / 100 |
| (1) | 0.2 / 0.02 | 100 / 100 |
| (11) | 0.2 / 0.02 | 100 / 100 |
| (20) | 0.2 / 0.02 | 100 / 90 |
| (12) | 0.2 / 0.02 | 100 / 80 |
| (10) | 0.2 / 0.02 | 100 / 40 |
| (35) | 0.2 / 0.02 | 100 / 90 |
| (36) | 0.2 / 0.02 | 100 / 90 |
| (37) | 0.2 | 100 |

Table 6-continued (LD₁₀₀ test/*Sitophilus granarius*)

| Active compound | Active compound concentration of the solution in % | Degree of destruction in % |
|---|---|---|
| (43) | 0.2 / 0.02 | 100 / 90 |
| (5) | 0.2 / 0.02 | 100 / 80 |
| (15) | 0.2 / 0.02 | 100 / 100 |
| (14) | 0.2 / 0.02 | 100 / 100 |
| (16) | 0.2 / 0.02 | 100 / 100 |
| (46) | 0.2 | 100 |
| (30) | 0.2 / 0.02 | 100 / 60 |
| (31) | 0.2 | 100 |
| (53) | 0.2 / 0.02 | 100 / 100 |
| (60) | 0.2 / 0.02 | 100 / 100 |

Table 6-continued
(LD$_{100}$ test/*Sitophilus granarius*)
| Active compound | Active compound concentration of the solution in % | Degree of destruction in % |
|---|---|---|
| 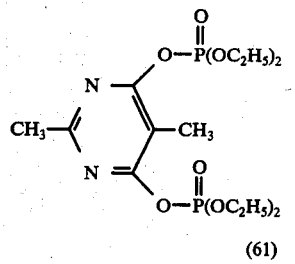 (61) | 0.2 | 100 |
| 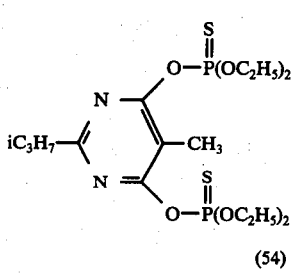 (54) | 0.2 | 100 |
| 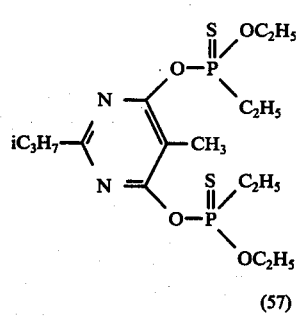 (57) | 0.2 | 100 |
| 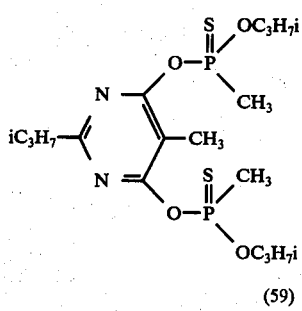 (59) | 0.2 | 100 |
| 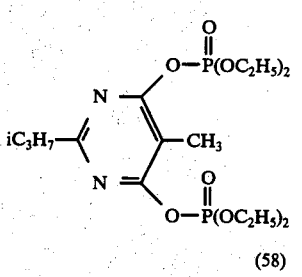 (58) | 0.2 | 100 |
Table 6-continued
(LD$_{100}$ test/*Sitophilus granarius*)
| Active compound | Active compound concentration of the solution in % | Degree of destruction in % |
|---|---|---|
| 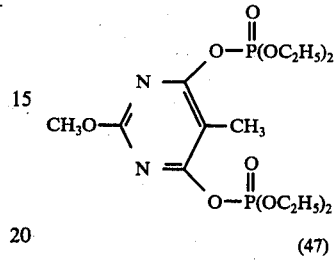 (47) | 0.2<br>0.02 | 100<br>90 |
| 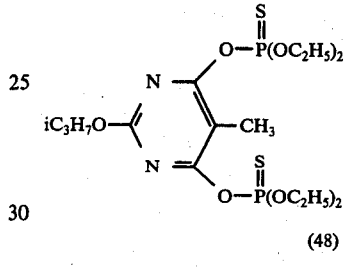 (48) | 0.2 | 100 |
| 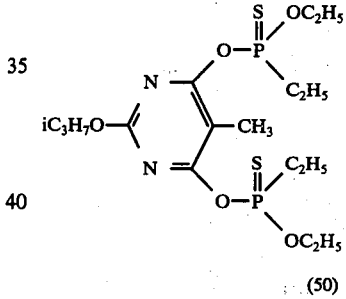 (50) | 0.2 | 100 |
| 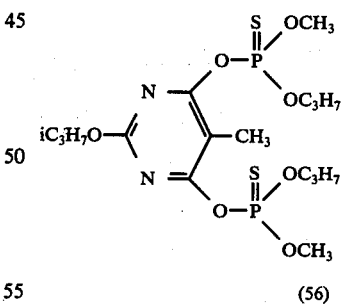 (56) | 0.2 | 100 |
| 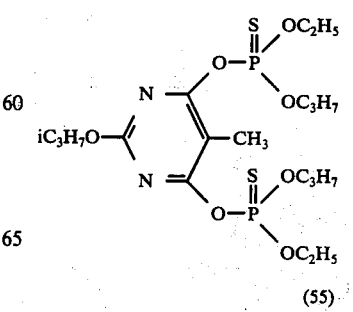 (55) | 0.2 | 100 |

Table 6-continued
(LD$_{100}$ test/*Sitophilus granarius*)

| Active compound | Active compound concentration of the solution in % | Degree of destruction in % |
|---|---|---|
| (51) | 0.2 | 100 |
| (49) | 0.2 | 100 |
| (52) | 0.2 / 0.02 | 100 / 80 |
| (64) | 0.2 / 0.02 | 100 / 100 |
| (65) | 0.2 | 100 |
| (17) | 0.2 / 0.02 | 100 / 80 |
| (18) | 0.2 | 100 |
| (2) | 0.2 / 0.02 | 100 / 100 |
| (62) | 0.2 | 100 |
| (63) | 0.2 | 100 |

The following further examples are set forth to illustrate, without limitation, the manner of producing the instant compounds according to the present invention:

EXAMPLE 7 a)

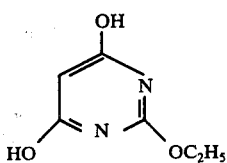

124.5 g (1 mole) of O-ethyl-isourea hydrochloride were added to a solution of 204 g (3 moles) of sodium ethylate in 1 l of ethanol at 0°–5° C. 160 g (1 mole) of malonic acid diethyl ester were then allowed to run in, without cooling, and the mixture is stirred for 3 hours at 60° C. The solvent was then distilled off in vacuo; the residue was dissolved in warm water. The solution was brought to about pH 3 by adding hydrochloric acid; it was then cooled to 0°–5° C and the product which had precipitated was filtered off. This gave 103 g (66% of theory) of 2-ethoxy-4,6-dihydroxypyrimidine in the form of a colorless powder of melting point >250° C.

The following compounds of the formula

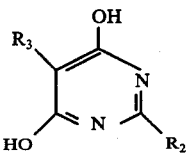

could be prepared analogously;

| $R_2$ | $R_3$ | Yield (% of theory) | Physical data (melting point, ° C) |
|---|---|---|---|
| —SH | H | 96 | >250 |
| —$C_3H_7$-iso | H | 58 | >250 |
| —$OCH_3$ | H | 80 | >300 |
| —$CH_3$ | H | 94 | >300 |
| —H | H | 56 | >300 |
| —C₆H₅ | H | 52 | >300 |
| —$C_2H_5$ | H | 96 | 301 (Decomposition) |
| —$OC_3H_7$-iso | H | 28 | >250 |
| —$OCH_3$ | $H_3C$— | 29 | 235 |
| —$OC_3H_7$-iso | $H_3C$— | 81 | 237 |
| —$CH_3$ | $H_3C$— | 95 | >250 |
| —$CH_3$ | Cl— | 81 | >250 |
| —$C_3H_7$-iso | $H_3C$— | 84 | >250 |

(b)

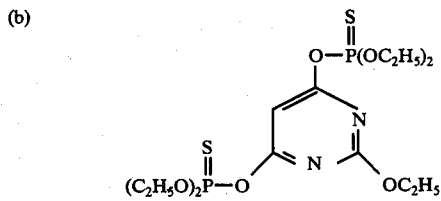

A mixture of 15.6 g (0.1 mole) of 2-ethoxy-4,6-dihydroxypyrimidine, 34.5 g (0.25 mole) of potassium carbonate, 200 ml of acetonitrile and 37.7 g (0.2 mole) of O,O-diethyl-thionophosphoric acid diester chloride was stirred for 13 hours at 45° to 50° C. 400 ml of toluene were then added to the reaction mixture, and the whole was washed with twice 300 ml of water. The organic phase was dried over sodium sulfate and the solvent was then distilled off in vacuo. The residue was subjected to slight distillation. This gave 35.8 g (78% of theory) O,O,O',O'-tetraethyl-O,O'-[2-ethoxy-pyrimidine-(4,6)-diyl]-bis-thionophosphoric acid ester in the form of a yellow oil of refractive index $n_D^{20}$: 1.5060.

EXAMPLE 8 a)

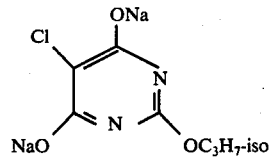

69 g (0.5 mole) of O-isopropylisourea hydrochloride were added to a solution of 102 g (1.5 moles) of sodium ethylate in 750 ml of ethanol at 0°–5° C and 97.5 g (0.5 mole) of chloromalonic acid diethyl ester were then added dropwise at 20° C. The mixture was warmed to 50° C for 8 hours and the solvent was then stripped off in vacuo. The residue was digested with hot acetonitrile and then dried. 157 g of a mixture of sodium chloride and the disodium salt of 5-chloro-2-isopropoxy-4,6-dihydroxypyrimidine, of melting point >300° C, were obtained.

b)

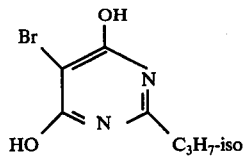

16 g (0.1 mole) of bromine were added dropwise to a solution of 15.4 g (0.1 mole) of 2-isopropyl-4,6-dihydroxypyrimidine and 5 g (0.125 mole) of sodium hydroxide in 150 ml of water, with slight cooling, so that the temperature remained below 40° C. The mixture was then stirred for a further half-hour without cooling, after which the product which had precipitated was filtered off. This gave 12 g (51% of theory) of 2-isopropyl-5-bromo-4,6-dihydroxypyrimidine as a colorless powder of melting point >250° C.

c)

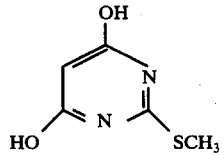

25.2 g (0.2 mole) of dimethyl sulfate were added to a solution of 28.8 g (0.2 mole) of 2-mercapto-4,6-dihydroxypyrimidine and 16.8 g (0.2 mole) of sodium bicarbonate in 400 ml of water. The mixture was stirred for a further hour at room temperature and the product which had precipitiated was then filtered off. This gave 10.3 g (33% of theory) of 2-methylmercapto-4,6-dihydroxypyrimidine in the form of a pink-colored powder of melting point >250° C.

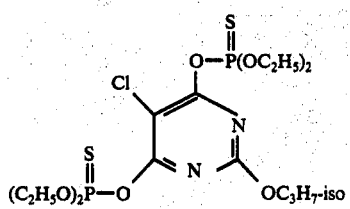

(2)

d. 37.6 g (0.2 mole) of O,O-diethylthionophosphoric acid diester chloride were added dropwise to 40 g of the disodium salt of 2-isopropoxy-5-chloro-4,6-dihydroxy-pyrimidine, containing some sodium chloride per (a) above, in 200 ml of acetonitrile at 20° C. The reaction mixture was allowed to react for 12 hours at 40° C and was then cooled and poured into 300 ml of toluene. The toluene solution was washed with saturated sodium carbonate solution and water and was then dried over sodium sulfate. After the solvent had been stripped off, the residue was subjected to slight distillation. 35 g of O,O,O',O'-tetraethyl-O,O'-[2-isopropoxy-5-chloropyrimidine (4,6)diyl]-bis-thionophosphoric acid ester were obtained in the form of a yellow oil of refractive index $n_D^{22}$: 1.5739. The following compounds of the formula

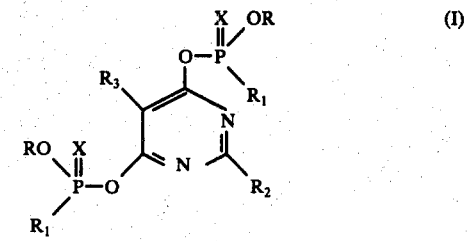

(I)

were prepared analogously:

Table 7

| Compound No. | R | $R_1$ | $R_2$ | $R_3$ | X | Yield (% of theory) | Physical data (refractive index, melting point, ° C) |
|---|---|---|---|---|---|---|---|
| 3 | $C_2H_5-$ | $C_2H_5O-$ | $-C_3H_7$-iso | H | S | 57 | $n_D^{23}$:1.4918 |
| 4 | $C_2H_5-$ | $C_2H_5-$ | $-C_3H_7$-iso | H | S | 86 | $n_D^{22}$:1.5237 |
| 5 | $C_2H_5-$ | $C_2H_5O-$ | $-SCH_3$ | H | S | 63 | $n_D^{21}$:1.5300 |
| 6 | $C_2H_5-$ | $C_2H_5-$ | $-C_3H_7$-iso | H | S | 69 | $n_D^{23}$:1.5805 |
| 7 | $C_2H_5-$ | $C_2H_5O-$ | $-C_3H_7$-iso | H | O | 80 | $n_D^{23}$:1.4657 |
| 8 | $C_2H_5-$ | $C_3H_7S-$ | $-C_3H_7$-iso | H | S | 68 | $n_D^{23}$:1.5454 |
| 9 | iso-$C_3H_7-$ | $CH_3-$ | $-C_3H_7$-iso | H | S | 63 | $n_D^{23}$:1.5158 |
| 10 | $C_2H_5-$ | $C_2H_5O-$ | $-OC_2H_5$ | H | O | 76 | $n_D^{23}$:1.4665 |
| 11 | $C_2H_5-$ | $C_2H_5-$ | $-OC_2H_5$ | H | S | 74 | $n_D^{23}$:1.5310 |
| 12 | iso-$C_3H_7-$ | $CH_3-$ | $-OC_2H_5$ | H | S | 74 | $n_D^{23}$:1.5248 |
| 13 | $C_2H_5-$ | $C_3H_7S-$ | $-OC_2H_5$ | H | S | 61 | $n_D^{23}$:1.5524 |
| 14 | $C_2H_5-$ | $C_2H_5-$ | $-SCH_3$ | H | S | 74 | $n_D^{23}$:1.5474 |
| 15 | iso-$C_3H_7-$ | $CH_3-$ | $-SCH_3$ | H | S | 74 | $n_D^{23}$:1.5397 |
| 16 | $C_2H_5-$ | $C_2H_5O-$ | $-SCH_3$ | H | O | 60 | $n_D^{23}$:1.4957 |
| 17 | $C_2H_5-$ | $C_2H_5O-$ | $-C_3H_7$-iso | Br | S | 64 | $n_D^{23}$:1.5132 |
| 18 | $C_2H_5-$ | $C_2H_5-$ | $-C_3H_7$-iso | Br | S | 69 | $n_D^{23}$:1.5335 |
| 19 | $CH_3-$ | $CH_3O-$ | $-OC_2H_5$ | H | S | 36 | $n_D^{20}$:1.5279 |
| 20 | $C_2H_5-$ | n-$C_3H_7O-$ | $-OC_2H_5$ | H | S | 41 | $n_D^{21}$:1.5080 |
| 21 | $C_2H_5-$ | $C_2H_5O-$ | $-OCH_3$ | H | S | 22 | $n_D^{18}$:1.5120 |
| 22 | $C_2H_5-$ | $C_2H_5-$ | $-OCH_3$ | H | S | 60 | $n_D^{18}$:1.5290 |
| 23 | $C_2H_5-$ | $C_2H_5-$ | $-CH_3$ | H | S | 57 | $n_D^{19}$:1.5242 |
| 24 | $C_2H_5-$ | $C_2H_5-$ | $-H$ | H | S | 61 | $n_D^{19}$:1.5279 |
| 25 | $C_2H_5-$ | $C_2H_5O-$ | H | H | S | 31 | $n_D^{19}$:1.5062 |
| 26 | $CH_3-$ | $C_2H_5-$ | $-OCH_3$ | H | S | 66 | $n_D^{21}$:1.5402 |
| 27 | iso-$C_3H_7-$ | $CH_3-$ | $-OCH_3$ | H | S | 67 | $n_D^{21}$:1.5230 |
| 28 | $C_2H_5-$ | $C_2H_5O-$ | $-CH_3$ | H | S | 35 | $n_D^{18}$:1.5040 |
| 29 | $CH_3-$ | $C_2H_5-$ | $-CH_3$ | H | S | 41 | $n_D^{18}$:1.5308 |
| 30 | $C_2H_5-$ | $C_2H_5O-$ |  | H | S | 68 | 44 |
| 31 | $C_2H_5-$ | $C_2H_5-$ |  | H | S | 76 | $n_D^{21}$:1.3662 |
| 32 | iso-$C_3H_7-$ | $CH_3-$ |  | H | S | 67 | 82 |
| 33 | $CH_3-$ | $CH_3O-$ | $-C_3H_7$-iso | H | S | 65 | $n_D^{21}$:1.5200 |
| 34 | n-$C_3H_7-$ | $C_2H_5-$ | $-CH_3$ | H | S | 42 | $n_D^{21}$:1.5240 |
| 35 | $C_2H_5-$ | $C_2H_5O-$ | $-OC_3H_7$-iso | H | S | 40 | $n_D^{21}$:1.5064 |
| 36 | $C_2H_5-$ | $C_2H_5-$ | $-OC_3H_7$-iso | H | S | 60 | $n_D^{21}$:1.5265 |
| 37 | iso-$C_3H_7-$ | $CH_3-$ | $-OC_3H_7$-iso | H | S | 57 | $n_D^{21}$:1.5200 |
| 38 | $C_2H_5-$ | $C_2H_5-$ | $-C_2H_5$ | H | S | 64 | $n_D^{20}$:1.5203 |
| 39 | iso-$C_3H_7-$ | $CH_3-$ | $-C_2H_5$ | H | S | 45 | $n_D^{20}$:1.5164 |
| 40 | $CH_3-$ | $C_2H_5O-$ | $-C_2H_5$ | H | S | 35 | $n_D^{20}$:1.5060 |
| 41 | $CH_3-$ | $CH_3O-$ | $-C_2H_5$ | H | S | 59 | $n_D^{19}$:1.5200 |
| 42 | $C_2H_5-$ | $C_2H_5O-$ | $-C_2H_5$ | H | S | 52 | $n_D^{19}$:1.5051 |
| 43 | $CH_3-$ | $CH_3O-$ | $-SCH_3$ | H | S | 59 | $n_D^{22}$:1.5583 |
| 44 | $CH_3-$ | $CH_3O-$ | $-CH_3$ | H | S | 31 | $n_D^{22}$:1.5266 |
| 45 | $CH_3-$ | $CH_3O-$ | $-H$ | H | S | 29 | $n_D^{22}$:1.5120 |
| 46 | $CH_3-$ | $CH_3O-$ |  | H | S | 49 | 63 |
| 47 | $C_2H_5-$ | $C_2H_5O-$ | $-OCH_3$ | $H_3C-$ | S | 64 | $n_D^{20}$:1.5061 |
| 48 | $C_2H_5-$ | $C_2H_5O-$ | $-OC_3H_7$-iso | $H_3C-$ | S | 73 | $n_D^{20}$:1.5071 |
| 49 | $C_2H_5-$ | $C_2H_5O-$ | $-OC_3H_7$-iso | $H_3C-$ | O | 65 | $n_D^{20}$:1.4723 |
| 50 | $C_2H_5-$ | $C_2H_5-$ | $-OC_3H_7$-iso | $H_3C-$ | S | 76 | $n_D^{20}$:1.5130 |
| 51 | $C_2H_5-$ | n-$C_3H_7S-$ | $-OC_3H_7$-iso | $H_3C-$ | S | 69 | $n_D^{20}$:1.5450 |
| 52 | $C_2H_5-$ | $C_2H_5O-$ | $-CH_3$ | Cl | S | 42 | 41 |
| 53 | $C_2H_5-$ | $C_2H_5O-$ | $-CH_3$ | $H_3C-$ | S | 29 | $n_D^{20}$:1.4962 |
| 54 | $C_2H_5-$ | $C_2H_5O-$ | $-C_3H_7$-iso | $H_3C-$ | S | 76 | $n_D^{20}$:1.5017 |

Table 7-continued

| Compound No. | R | R₁ | R₂ | R₃ | X | Yield (% of theory) | Physical data (refractive index, melting point, °C) |
|---|---|---|---|---|---|---|---|
| 55 | $C_2H_5-$ | $n-C_3H_7O-$ | $-OC_3H_7$-iso | $H_3C-$ | S | 48 | $n_D^{20}$:1.5069 |
| 56 | $CH_3-$ | $n-C_3H_7O-$ | $-OC_3H_7$-iso | $H_3C-$ | S | 80 | $n_D^{20}$:1.5060 |
| 57 | $C_2H_5-$ | $C_2H_5-$ | $-C_3H_7$-iso | $H_3C-$ | S | 64 | $n_D^{20}$:1.5229 |
| 58 | $C_2H_5-$ | $C_2H_5O-$ | $-C_3H_7$-iso | $H_3C-$ | O | 45 | $n_D^{20}$:1.4609 |
| 59 | iso-$C_3H_7-$ | $CH_3-$ | $-C_3H_7$-iso | $H_3C-$ | S | 75 | partially crystalline |
| 60 | $C_2H_5-$ | $C_2H_5-$ | $-CH_3$ | $H_3C-$ | S | 61 | $n_D^{20}$:1.5160 |
| 61 | $C_2H_5-$ | $C_2H_5O-$ | $-CH_3$ | $H_3C-$ | O | 53 | $n_D^{20}$:1.4396 |
| 62 | $C_2H_5-$ | $C_2H_5-$ | $-OC_3H_7$-iso | Cl | S | 42 | $n_D^{20}$:1.5226 |
| 63 | $C_2H_5-$ | $C_2H_5O-$ | $-OC_3H_7$-iso | Cl | O | 35 | $n_D^{20}$:1.4516 |
| 64 | $C_2H_5-$ | $C_2H_5-$ | $-CH_3$ | Cl | S | 71 | $n_D^{19}$:1.5172 |
| 65 | $C_2H_5-$ | $C_2H_5O-$ | $-CH_3$ | Cl | O | 51 | $n_D^{19}$:1.4473 |
| 66 | iso-$C_3H_7-$ | $CH_3-$ | $-CH_3$ | H | S | 70 | $n_D^{20}$:1.5190 |
| 67 | iso-$C_3H_7-$ | $CH_3-$ | $-H$ | H | S | 73 | $n_D^{20}$:1.5268 |
| 68 | $CH_3-$ | $C_2H_5-$ | $-SCH_3$ | H | S | 77 | $n_D^{22}$:1.5717 |
| 69 | $C_2H_5-$ | $CH_3-$ | $-SCH_3$ | H | S | 77 | $n_D^{22}$:1.5639 |
| 70 | $CH_3-$ | $C_2H_5-$ | $-C_2H_5$ | H | S | 65 | $n_D^{22}$:1.5338 |
| 71 | $C_2H_5-$ | $CH_3-$ | $-C_2H_5$ | H | S | 68 | $n_D^{22}$:1.5255 |
| 72 | $C_2H_5-$ | $CH_3-$ | $-CH_3$ | H | S | 60 | 77 |
| 73 | $(CH_3)_2CH-CH_2-$ | $C_2H_5-$ | $-CH_3$ | H | S | 70 | $n_D^{20}$:1.5117 |
| 74 | $CH_3-$ | $C_2H_5-$ | H | H | S | 62 | 63 |
| 75 | $C_2H_5-$ | $CH_3-$ | H | H | S | 53 | $n_D^{21}$:1.5405 |
| 76 | $n-C_3H_7-$ | $C_2H_5-$ | H | H | S | 65 | $n_D^{21}$:1.5347 |
| 77 | $(CH_3)_2CH-CH_2-$ | $C_2H_5-$ | H | H | S | 66 | $n_D^{21}$:1.5105 |
| 78 | $CH_3-$ | $n-C_3H_7O-$ | $-C_3H_7$-iso | H | S | 74 | $n_D^{21}$:1.5062 |
| 79 | $CH_3-$ | $C_2H_5-$ | $-C_3H_7$-iso | H | S | 73 | $n_D^{21}$:1.5328 |
| 80 | $C_2H_5-$ | $n-C_3H_7O-$ | $-C_3H_7$-iso | H | S | 68 | $n_D^{21}$:1.5028 |
| 81 | $CH_3-$ | $C_2H_5-$ | $-OC_2H_5$ | H | S | 62 | $n_D^{23}$:1.5409 |
| 82 | $C_2H_5-$ | $CH_3-$ | $-OC_2H_5$ | H | S | 75 | $n_D^{23}$:1.5349 |
| 83 | $n-C_3H_7-$ | $C_2H_5-$ | $-C_3H_7$-iso | H | S | 66 | $n_D^{23}$:1.5225 |
| 84 | iso-$C_3H_7-$ | $C_2H_5-$ | $-C_3H_7$-iso | H | S | 57 | $n_D^{23}$:1.5241 |
| 85 | $C_2H_5-$ | $CH_3-$ | $-C_3H_7$-iso | H | S | 80 | $n_D^{23}$:1.5240 |
| 86 | $(CH_3)_2CH-CH_2-$ | $C_2H_5-$ | $-C_3H_7$-iso | H | S | 79 | $n_D^{23}$:1.5060 |

It will be appreciated that the instant specification and examples are set forth by way of illustration and not limitation, and that various modifications and changes may be made without departing from the spirit and scope of the present invention.

What is claimed is:

1. A pyrimidine (4,6)diyl-bis-(thiono) (thiol)-phosphoric (phosphonic) acid ester of the formula

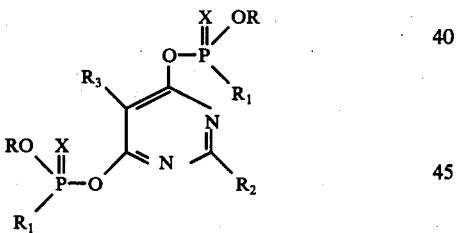

in which
R is alkyl with 1 to 6 carbon atoms,
R₁ is alkyl, alkoxy or alkylmercapto each with 1 to 6 carbon atoms or phenyl,
R₂ is alkyl, alkoxy or alkylmercapto each with 1 to 5 carbon atoms, hydrogen or phenyl,
R₃ is hydrogen, alkyl with 1 to 4 carbon atoms or halogen, and
X is oxygen or sulfur.

2. A compound according to claim 1, in which R is alkyl with 1 to 5 carbon atoms, R₁ is alkyl, alkoxy or alkylmercapto each with 1 to 5 carbon atoms or phenyl, R₂ is alkyl, alkoxy or alkylmercapto each with 1 to 4 carbon atoms, hydrogen or phenyl, and R₃ is hydrogen, alkyl with 1 to 3 carbon atoms, fluorine, chlorine, bromine or iodine.

3. The compound according to claim 1, wherein such compound is O,O,O',O'-tetraethyl-0,0'-[2-isopropyl-pyrimidine-(4,6)-diyl]-bis-thionophosphoric acid ester of the formula

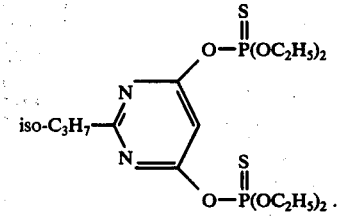

4. The compound according to claim 1, wherein such compound is O,O'-diisopropyl-O,O'-[2-isopropyl-pyrimidine-(4,6)-diyl]-bis-methanethionophosphonic acid ester of the formula

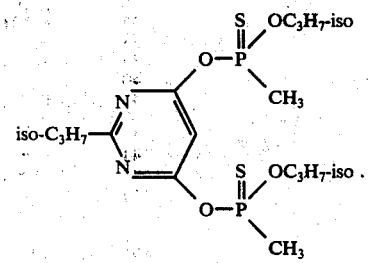

5. The compound according to claim 1, wherein such compound is O,O,O',0'-tetramethyl-O,O'-[2-ethoxy-pyrimidine-(4,6)-diyl]-bis-thionophosphoric acid ester of the formula

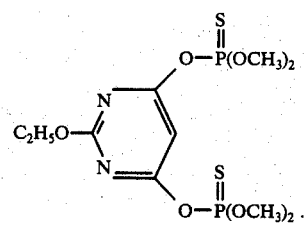

6. The compound according to claim 1, wherein such compound is O,O'-diethyl-O,O'-[2-methyl-pyrimidine-(4,6)-diyl]-bis-ethanethionophosphonic acid ester of the formula

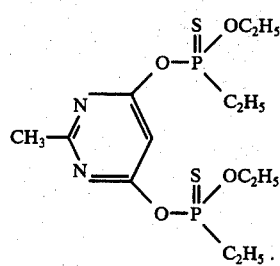

7. The compound according to claim 1, wherein such compound is O,O,O',O'-tetramethyl-O,O'-[2-isopropyl-pyrimidine-(4,6)-diyl]-bis-thionophosphoric acid ester of the formula

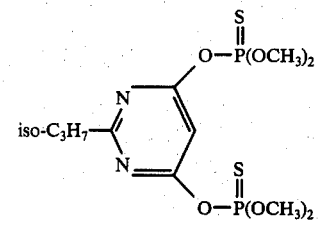

8. An insecticidal or acaricidal composition containing as active ingredient an insecticidally or acaricidally effective amount of a compound according to claim 1 in admixture with a diluent.

9. A method of combating insects or acarid pests which comprises applying to the pests or a habitat thereof an insecticidally or acaricidally effective amount of a compound according to claim 1.

10. The method according to claim 9 in which said compound is
O,O,O',O'-tetraethyl-O,O'-[2-isopropyl-pyrimidine-(4,6)-diyl]-bis-thionophosphoric acid ester,
O,O'-diisopropyl-O,O'-[2-isopropyl-pyrimidine-(4,6)-bis-yl]-dimethanethionophosphonic acid ester,
O,O,O',O'-tetramethyl-O,O'-[2-ethoxy-pyrimidine-(4,6)-diyl]-bis-thionophosphoric acid ester,
O,O'-diethyl-O,O'-[2-methyl-pyrimidine-(4,6)-diyl]-bis-ethanethionophosphonic acid ester or
O,O,O',O'-tetramethyl-O,O'-[2-isopropyl-pyrimidine-(4,6)-diyl]-bis-thionophosphoric acid ester.

* * * * *